Figure 1:
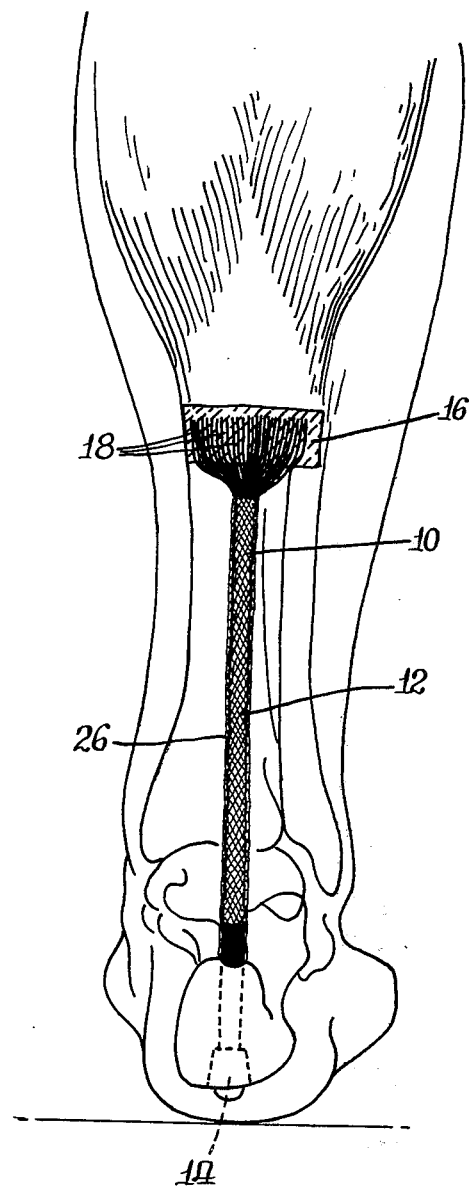

United States Patent [19]

Bokros

[11] 4,149,277
[45] Apr. 17, 1979

[54] ARTIFICIAL TENDON PROSTHESES

[75] Inventor: Jack C. Bokros, San Diego, Calif.

[73] Assignee: General Atomic Company, San Diego, Calif.

[21] Appl. No.: 808,868

[22] Filed: Jun. 22, 1977

[51] Int. Cl.² ............................................. A61F 1/00
[52] U.S. Cl. ............................................. 3/1; 3/1.9
[58] Field of Search .................... 3/1, 1.9; 128/334 R

[56] References Cited

U.S. PATENT DOCUMENTS

| | | | |
|---|---|---|---|
| 3,176,316 | 4/1965 | Bodell | 3/1 |
| 3,745,590 | 7/1973 | Stubstad | 3/1.9 |
| 3,952,334 | 4/1976 | Bokros et al. | 3/1 |
| 3,973,277 | 8/1976 | Semple | 3/1 |
| 3,992,725 | 11/1976 | Homsy | 3/1 |
| 4,064,566 | 12/1977 | Fletcher | 3/1.9 |
| 4,084,266 | 4/1978 | Polrier et al. | 3/1 |

OTHER PUBLICATIONS

"Filamentous Carbon Fibre as a Tendon Prosthesis" D. Jenkins, paper 114, Eighth Annual International Biomaterials Symposium, Apr. 9-13, 1976.

"Results of Animal & Clinical Studies with novel Prostheses for Ligaments & Tendons," C. Homsy, et al., paper No. 113, Eighth Annual International Biomaterials Symposium, Apr. 9-13, 1976.

*Primary Examiner*—E. H. Eickholt
*Attorney, Agent, or Firm*—Fitch, Even & Tabin

[57] ABSTRACT

Biocompatible artificial tendon or ligament prostheses having an exterior adherent coating of vapor deposited carbon, comprising a strand of a plurality of fibers each of which is designed to sustain a tensile strain of about 5 percent or less and means for attaching the strand at the implantation site.

3 Claims, 3 Drawing Figures

U.S. Patent  Apr. 17, 1979  4,149,277

ARTIFICIAL TENDON PROSTHESES

The present invention relates to prosthetic devices, and more particularly is directed to artificial tendon or ligament prostheses utilizing a vapor deposited carbon coating.

The employment of pyrolytic carbon coatings to produce biocompatible and thromboresistant surfaces for prosthetic devices is known and is described in U.S. Pat. No. 3,526,005 issued Sept. 1, 1970 and U.S. Pat. No. 3,685,059, issued Aug. 22, 1972. These patents generally describe deposition of pyrolytic carbon coatings, usually from a diluted hydrocarbon atmosphere at atmospheric pressure. Various other techniques have been developed for depositing carbon coatings, for example as by vacuum vapor deposition (VVD) which is also sometimes referred to as vacuum metalizing, physical vapor deposition or evaporative coating, sputtering, or as by ion-plating techniques [e.g., see Marinkovic, et al., Carbon, 14, 329 (1976); cited references are incorporated herein by reference]. Coatings deposited by such VVD or ion-plating techniques have been utilized in prosthetic devices, as described in U.S. Pat. No. 3,952,334. However, despite these advances, there are still deficiencies in the provision of certain prosthetic elements such as artificial tendon or ligament replacements. In this connection, the variety of tendon replacement methods may be considered to indicate the generally unsatisfactory present state of the art. [D. Jenkins, *Filamentous Carbon Fibre as a Tendon Prosthesis*, Paper 114, Final Program of the Second Annual Meeting of the Society for Biomaterials in conjunction with the Eighth Annual International Biomaterials Symposium, Apr. 9–13, 1976]. With the exception of tendon autografts most conventional tendon replacement systems rely on the use of an artificial fiber to take the place of the tendon.

Artificial prostheses for ligaments and tendons have evolved from various animal and clinical studies and exhibit some common features: (a) stress bearing core structures which exhibit elastic behavior analogous to natural ligament and tendon structures; (b) initial fixation means to allow the early mobilization of involved natural structures; and (c) anastomatic engagement with living tissue through tissue ingrowth mechanisms. [*Results of Animal and Clinical Studies with Novel Prostheses for Ligaments and Tendons*, Charles A. Homsy, et al., Paper No. 113, Final Program of the Second Annual Meeting of the Society for Biomaterials in conjunction with the Eighth Annual International Biomaterials Symposium, Apr. 9–13, 1976].

In order for such a replacement to be entirely satisfactory the new "tendon" must be biologically inert and yet be strong and pliable. Artificial tendon and ligament prostheses have been made from filamentous carbon fibers in view of their inertness, strength and pliability, in order to provide temporary replacement of the absent tendon. It has been further reported that filamentous carbon fibers encourage tissue ingrowth, not only from the ends but also throughout the length of the implant in such a manner that it acts as a scaffold into which new fibrous tissues can grow. Normal tissue is said to rapidly take over from the implant, with a rapid increase in strength of the implant as it becomes invaded with new tissue. Thus, the stress-strain characteristic of the initial scaffolding material is of lesser importance; the mechanical behavior of the newly formed tendon or liagment will be determined primarily by the tissue.

However, in conventional applications of filamentous carbon in the replacement of large tendon defects, the carbon filaments have been found to break up and migrate to the vital organs. [*Filamentous Carbon Fibre as an Orthopaedic Implant Material*, D. Jenkins, et al., Problems of Biocompatibility, 1976; D. Wolter, et al., 3rd Annual Meeting of the Society for Biomaterials 9th Annual International Biomaterials Symposium, Paper 119, New Orleans] Further in this connection, while the use of such fibers as replacements for lateral knee ligaments, tendon achilles and cruciate ligaments in animal studies has shown that such fibers are accepted by tissues and promote the formation (in a tendon substitute) of a new tendon-like tissue of correct bulk, cell type and alignment, there are problems with prolonged or permanent implantation. In this connection, the carbon only maintains its strength for several months, than gradually fragments, and is subsequently collected in the regional nodes. Thus, despite development effort in respect to artificial tendon replacements, wholly satisfactory tendon replacements for prolonged or permanent implantation in a living body are not conventionally available.

Figure 2:
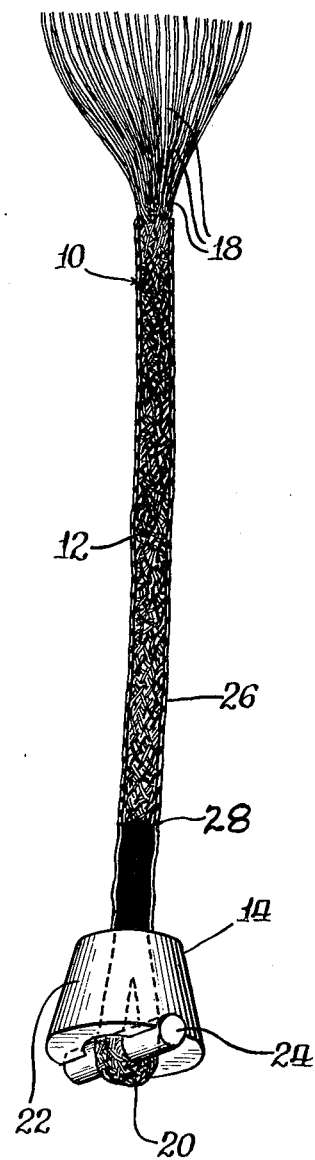
Figure 3:
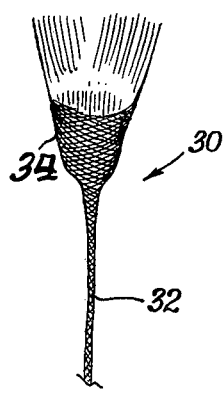

It is the object of the present invention to provide for artificial tendon prostheses which are suitable for prolonged or permanent implantation in a living body. This and other objects of the invention will be readily apparent from the following detailed description and the accompanying drawings of which FIG. 1 is a perspective view of one embodiment of an artificial tendon replacement in accordance with the present invention;

FIG. 2 is a cross sectional view of the tendon replacement of FIG. 1 taken through line 1—1; and FIG. 3 is an illustration of another embodiment of an artificial tendon prostheses in accordance with the present invention.

Generally, the present invention is directed to artificial tendon or ligament prostheses for prolonged or permanent implantation in a living body. The prostheses comprise an elongated, flexible, carbon-coated strand itself comprising a plurality of fibers of particular characteristics.

The flexible strand element comprises a plurality of organo polymeric fibers of relatively small diameter which are able to sustain the functional stresses intended for the prostheses without individually straining more than about 5 percent. Depending on the weave employed, strains in excess of 5 percent may be sustained by the whole ligament or tendon. The fibers should generally best have a major diameter dimension of less than about 25 microns, and a minor diameter dimension of at least about 5 microns, although fibers as small as 1 micron might be used in certain applications. By "major diameter dimension" is meant the widest dimension of the fiber in a direction orthogonal to the longitudinal axis of the fiber, and by "minor diameter dimension" is meant the narrowest dimension of the fiber in a direction orthogonal to the longitudinal axis of the fiber. Of course, for a fiber of circular cross-section, the major and minor dimensions will be the same, but it should be appreciated that the invention does contemplate fibers of non-circular cross-section.

The carbon-coated prosthetic strands of the present invention have a relatively high degree of flexibility, which is due primarily to bending of the fibers. The radius or curvature of the individual fibers that will be allowed is determined only by the radius of the fiber. The radius of curvature is:

$$R = (\text{Radius/allowable strain} = 5\%)$$

For a radius of 10 microns ($=10^{-3}$ cm), the allowable radius R is:

$$R = (10^{-3}/0.05) = (10^{-1}/5) = 0.02 \text{ cm}.$$

The relatively small fiber diameters provide the prosthetic fiber fabrics with substantial flexibility without cracking the coating, which can withstand at least about 5% strain. Smaller fibers are preferred for increased flexibility, and the lower limit of diameter is determined by the handling and coating parameters.

The organo polymeric fibers should also be of a material having a tensile strength of at least about 20,000 psi and should be fabricated of biocompatible medical grade materials. Furthermore, the organo polymeric fibers should have a tensile modulus of elasticity of about $2 \times 10^5$ psi or more. Polyethylene terephthalate fibers, such as those sold under the trade name Dacron, are particularly preferred because of the biocompatibility of such polyester fibers ["Implants in Surgery", D. Williams, et al., W. B. Saunders Company, Ltd., London (1973)], their strength (e.g., 50,000 to 99,000 psi breaking strength) and stiffness (e.g., modulus of elasticity of about $2 \times 10^6$ psi) which is near that of an isotropic carbon coating. Such a high modulus, high strength material can support a large load without straining more than 5% (at which point the carbon coating will break). Polyethylene terephthalate fibers may be, for example, about three times tougher and five times stiffer than poly(tetrafluoroethylene).

The fibers are provided in a suitable array for the particular prostheses application, and may desirably be provided as a weave, mesh or braid. The array should be capable of providing for tissue ingrowth, so that the prostheses can serve as a scaffold for tissue reformation. In this connection, the structure should be loosely woven or arranged to provide spaces larger than about 100 microns for tissue ingrowth. Other suitable high strength high modulus organo polymeric substrate materials, provided their bio-compatibility is demonstrated, include various so-called "high temperature polymers" which have generally been developed in the last decade, aromatic polyimides, and aromatic polyamides.

As indicated, the flexible strand of fibers is provided with an adherent carbon coating, and in this connection, carbon, the organic building block of all body matter, has shown outstanding tissue and blood compatibility for a variety of prosthetic device applications. Such carbon coatings may be provided by ion-plating, sputtering or VVD coating techniques, to produce strongly adherent carbon coatings which provide a particularly desirable biomedical interface between the prosthesis and the implantation site. The fibers may be aligned, braided, or woven in the flexible strand tensile element. The fibers will typically be about 10 microns in diameter. The smaller the fiber, the smaller the radius of curvature it can sustain without cracking the carbon coating which can sustain at least about 5% elastic strain before fracture, as previously discussed. In view of the small diameter of the fibers used, it is a desirable advantage that the carbon coating may be provided either by coating the individual fibers or yarn, or by coating the assembled strand array. High temperature polymers, which may be used in fiber or metal coating application herein exhibit thermal stability at temperatures of 300° C. and higher and are generally characterized as high temperature, high molecular weight, aromatic, nitrogen-linked polymers. Such polymers are well known in the polymer art, and examples of such high-temperature polymers include ordered aromatic copolyamides, such as the reaction product of phenylenebis (amino-benzamide) and isophthaloyl chloride, all-aromatic polybenzimidazoles, such as poly [2,2'(m-phenylene)-5,5' (6,6' benzimidazole)], polyozadiazoles, poly (n-phenyl triazoles), polybenzobenzimidazoles, polyimides and poly (amide-imide) resins. Of course, the biocompatibility of such fibers should be tested. The preferred organo polymeric fibers contemplated for use herein are medical grade polyethylene—terephthalates, but various conventional high temperature polymer fibers commercially available such as fibers sold under the name Kevlar by DuPont and having a modulus of about $10 \times 10^6$ psi may prove useful.

The tendon prostheses in accordance with the present invention can be used with a variety of suitable means for attachment at the implantation site. In this connection, at least one end of the tendon prostheses will usually be intended to be affixed to the skeletal structure. It will usually be desirable to provide means for affixation of the other end to soft body tissue such as muscle and/or remaining tendon tissue, although ligament prostheses may be joined to bone tissue at both ends of the prosthesis.

In connection with attachment, a variety of means and techniques may be used. For example, a plug/pin attachment system [e.g., Jenkins, et al., supra] or screw attachment system [e.g., Wolter, et al., supra] may be used. For attachment to soft tissue, a variety of suturing methods may be used [e.g., Amstutz, et al., J. Biomed. Mater. Res. 10, 48 (1976)]. Further in this connection, the prosthesis strand, or tissue-connecting portion of the strand, may be provided with a configuration such as a hollow braid structure which tightens under tensile load. A bone-anchoring means of the plug type should best have a modulus of elasticity approximating that of natural bones, although this is not a particularly desirable factor in respect of soft tissue affixation means. However, while it is desirable to have tissue affixation and/or firm anchoring of the ends of the tendon or ligament prostheses, it is usually undesirable to permit tissue adhesion or affixation to the central portion of the flexible strand element of the protheses, which should be relatively free to move in order to perform its function. A sheath such as a silicone sheath may be used to prevent attachment of the ligament or tendon to the surrounding tissue [Amstutz, et al., supra]. Such a sheath may also be provided with a carbon coating, and preferably will be coated on the inside of the sheath but not the outside.

As previously indicated, the entire prosthesis assembly, or individual parts thereof, are coated with a carbon layer. The carbon may be applied using coating technology, such as described in U.S. Pat. No. 3,952,334.

The carbon coating should be at least about 1000Å (0.1 micron) thick, should be adherent, and in order to provide for large fracture strains, should have BAF (Bacon Anisotropy Factor) of about 1.2 or less. Generally, a coating thickness of about 3,000 to about 5,000Å of dense carbon (at least about 1.6 gm/cm$^3$) is employed; greater thicknesses tend to crack and flake. Preferably, the vapordeposited carbon has a density of at least about 1.8 gm/cm$^3$. Such vapor-deposited carbon exhibits biocompatible properties and also may be provided with excellent adherence to the small polymer fibers of the flexible strand. As a result, the coated fibers exhibit excellent properties for use as a prosthetic device and are considered to be fully acceptable for implantation within the human body in flexible and tensile service in a permanent tendon or ligament replacement. Further, through the design provision for a limited tensile strain of not more than 5% for the individual fibers, the integrity of the carbon coating is preserved for prolonged or permanent implantation service. In this regard, as previously indicated, oriented polyethylene terephthalate fibers (e.g., medical grade Dacron) having a high stiffness and high strength are preferred. Other polymers such as aromatic polymers like Kevlar (tensile modulus of $10 \times 10^6$ psi) may also be useful in small fiber form. Thus, an artificial tendon or ligament replacement is provided which does not break up and migrate in the manner of conventional filamentous carbon fiber prostheses, and which is capable of providing a permanent scaffolding for the regeneration of new functional tissue.

Having generally described artificial tendon and ligament prosthesis in accordance with the present invention, the invention will now be more particularly described with respect to the embodiment illustrated in FIG. 1, which is a side view, partially broken away, of an artificial achilles tendon prosthesis 10 in position at the implantation site. The prosthesis 10 comprises a flexible strand element 12, a bone affixation element 14 at one end of the tendon strand element 12, and soft-tissue affixation means 16 at the other end of the central strand element 12. The bone affixation element 14 of the tendon prosthesis 10 is positioned in anchored relationship in the calcaneus at the implantation site, and the soft-tissue affixation means is in intergrowth affixation relationship to a remaining portion of the natural achilles tendon at the implantation site.

Turning now to FIG. 2 in which the implant 10 is shown in more detail, it may be seen that the flexible strand element 12 comprises a plurality of individual fibers 18 which are in braided relationship. The fibers are of circular cross-section and are made of axially oriented polyethylene terephthalate. The fibers have a diameter of about 10 microns, a tensile strength of about 40,000 psi and a tensile modulus of about $2 \times 10^6$ psi. The fibers of the strand 12 are braided, and form a loop 20 at the bone-joining means 14 of the tendon prosthesis. The bone-joining means 14 itself is composed of a pyrolytic carbon coated artificial graphite substrate plug 22 and a carbon coated metallic or graphite pin 24 which passes through the loop 20 to provide for tensile load transport to the plug element 22. The coated artificial graphite plug, which is made of a material such as POCO-AXF-5Q graphite, has modulus of elasticity approximating that of natural bone, in order to facilitate load transfer to the implantation attachment site. At the other end of the strand element 12 the fiber ends are affixed to a porous mesh material of Dacron by weaving to provide a structure into and through which new soft tissue may grow to provide for soft-tissue attachment. A removable silicone sheath 26, shown primarily in cross-section upwardly of numeral 28 and having a carbon coating on its inner surface adjacent the strand, is provided surrounding the central portion of the strand element.

The prosthesis has a dense carbon coating on the fibers and affixation means. The braided or woven strand may be coated, or the yarn from which the device is woven may be coated prior to weaving or braiding. In any event, the finished assembly is coated with a smooth layer of vapor deposited pyrolytic carbon having a BAF thickness of about 3000 Angstroms over the entire assembly 10. Upon implantation, the tendon prosthesis 10 is flexible and fatigue resistant, and resists tissue adhesion to permit relative mobility in the surrounding sheath of tissues and does not break up and migrate to regional nodes or vital organs. The smooth carbon surface is very inert and tissue does not bond to it chemically. The bone and soft-tissue affixation means at the respective ends of the prosthesis 10 provides for tissue ingrowth and firm attachment at the attachment sites upon tissue growth.

Illustrated in FIG. 3 is a partial side view of another embodiment of tendon prosthesis 30 which illustrates a self-tightening braid attachment to a severed tendon. In this connection, the prosthesis 30 comprises a strand 32 of Dacron fiber which is coated in an evaporative coater containing a crucible filled with a commercial grade of artificial graphite heated by electron bombardment. Coating is carried out until a thickness of about 4500 Angstroms of carbon is deposited. The carbon coating is smooth and uniform, and has a density of about 2.0 gm/cm$^3$. The strand 32 is in the form of a hollow braided tube, the diameter of which decreases as the tube is stretched, thus providing a tightening mechanism. The end 34 of the tube strand 32 is slipped over the free end of a severed tendon, and fixed in place by means of a number of sutures, where it will be retained by tissue growth.

It will be appreciated that in accordance with the present invention, artificial tendon or ligament prostheses have been provided which are particularly adapted for prolonged or permanent implantation in a living body, which are biologically inert, and which are capable of reestablishing muscular-skeletal tendon function.

Although the invention has been described with regard to certain preferred embodiments, it should be understood that modifications such as would be obvious to those having the ordinary skill in this art may be made without deviating from the scope of the invention which is defined in the appended claims.

Various of the features of the invention are set forth in the following claims.

What is claimed is:

1. An artificial tendon or ligament prostheses for prolonged or permanent implantation in a living body and adapted for service at a predetermined maximum tensile load, comprising
   an elongated, flexible strand comprising a plurality of substrate fibers having a tensile modulus of about $2 \times 10^6$ psi or more and capable of sustaining a tensile strain of about 5% or less at the maximum tensile load and having an adherent dense, isotropic carbon coating on said substrate fibers, and
   means for suitably attaching the tendon prostheses to living tissue.

2. A prostheses in accordance with claim 1 wherein said fibers are polyethylene terephthalate fibers having a diameter of about 25 microns or less, and wherein said carbon coating has a BAF of about 1.2 or less and a thickness in the range of from about 1000 Angstroms to about 5000 Angstroms.

3. A prostheses in accordance with claim 1 wherein said attachment means comprises a carbon coated bone affixation element attached at one end of said strand, and a carbon coating soft tissue affixation element at the other end of said strand.

* * * * *